United States Patent [19]
Koninckx

[11] Patent Number: 5,662,676
[45] Date of Patent: Sep. 2, 1997

[54] INSTRUMENT SET FOR LAPAROSCOPIC HYSTERECTOMY

[75] Inventor: Philippe Robert Koninckx, Bierbeek, Belgium

[73] Assignee: K.U. Leuven Research & Development, Leuven, Belgium

[21] Appl. No.: 356,370

[22] PCT Filed: Jun. 23, 1993

[86] PCT No.: PCT/BE93/00040

§ 371 Date: Mar. 7, 1995

§ 102(e) Date: Mar. 7, 1995

[87] PCT Pub. No.: WO94/00061

PCT Pub. Date: Jan. 6, 1994

[30] Foreign Application Priority Data

Jun. 24, 1992 [NL] Netherlands ............. 92.01118

[51] Int. Cl.[6] .................................... A61B 17/02
[52] U.S. Cl. ................. 606/198; 604/105; 600/210
[58] Field of Search ........................... 606/119, 191, 606/198, 20; 600/201, 210, 216; 604/104–110

[56] References Cited

U.S. PATENT DOCUMENTS 3,857,395 12/1974 Johnson et al. ............. 606/198
5,113,846  5/1992 Hiltebrandt et al. ......... 604/105
5,339,803  8/1994 Mayzels et al. ............. 606/198
5,351,679 10/1994 Mayzels et al. ............. 606/198

FOREIGN PATENT DOCUMENTS

WO8904188 11/1988 WIPO.

OTHER PUBLICATIONS

Reich et al., J. Gynaecol. Surg., 1989. 3 pages.

*Primary Examiner*—Michael Buiz
*Assistant Examiner*—William Lewis
*Attorney, Agent, or Firm*—Webb Ziesenheim Bruening Logsdon Orkin & Hanson, P.C.

[57] ABSTRACT

The invention relates to an instrument set for laparoscopic vaginal hysterectomy which comprises a uterine rotator comprising a rod with a uterine end for insertion into the uterus and a control end, and with at least one wing moveable in and out of the uterine end which in a folded-out position makes contact with the inner wall of the uterus and which is connected via coupling means to a control member located at the control end, wherein the rod is preferably provided with two wings, and more preferably the rod is provided with a hinge, and with optionally at least one artery forceps provided with a handle and mutually reciprocating jaws.

18 Claims, 8 Drawing Sheets

INSTRUMENT SET FOR LAPAROSCOPIC HYSTERECTOMY

BACKGROUND OF THE INVENTION

1. Field of the Invention

The present invention relates to an instrument set for laparoscopic hysterectomy, including laparoscope-assisted sub-total and total hysterectomy, and to a uterine rotator and an artery forceps therefor.

Hysterectomy is one of the surgical operations most frequently performed on women. On average the uterus is removed in one of three women.

SUMMARY OF THE INVENTION

Abdominal hysterectomy is generally performed in particular when the uterine volume is large, when extensive pelvic adhesions are present or expected, and when other pathology such as ovarian cysts, extensive endometriosis or cancer are present.

Vaginal hysterectomy has the advantage relative to abdominal hysterectomy of a lower post-operative morbidity and the absence of abdominal scars.

Endoscopic Surgery has been employed more and more in recent years due to technical developments in the area of video-endoscopy and in the area of lasers as bloodless, precision cutting instruments in addition to persufflation techniques, such as described in EP-A-0 350 499.

Laparoscopic hysterectomy has already been described by Reich et al., J. Gynaecol. Surg., 1989, 5, p. 213–216.

A frequently occurring problem, especially with a larger uterus, is that during the operation the uterus rotates spontaneously whereby the operation becomes more difficult. Problems can occur particularly at the most crucial moment of the operation, when the uterine artery is ligated. Moreover it can be necessary in the case of a myomatous uterus to rotate the uterus in order to expose the broad ligament and the uterine artery.

In order to facilitate laparoscopic vaginal hysterectomy, to shorten the operation time and to increase the percentage of successful operative procedures the present invention provides an instrument set. The instrument set for laparoscopic vaginal hysterectomy according to the invention is characterized in that it comprises a uterine rotator comprising a rod with a uterine end for insertion into the uterus and a control end, and with at least one wing movable in and out of the uterine end which in the folded-out position makes contact with the inner wall of the uterus and which connected via coupling means to a control member located at the control end. It is thus possible with the uterine rotator to fix the uterus and rotate it in controlled manner whereby the necessary surgical procedures viewed with a laparoscope can be optimally performed.

Fixed and controlled rotation of the uterus is further improved if more preferably the rod is provided with two wings which in that case are preferably movable diametrically relative to each other and in and out of the uterine end of the rod.

In order to provide a uterine rotator combining good fixed and controlled rotation of the uterus with a construction which can be prepared well in pro-operative instrument treatments such as sterilization and the like, each wing preferably comprises two wing portions connected for mutual rotation, whereof a first wing portion is rotatably connected to a rod tip and whereof the second wing portion is connected to the coupling means. When more preferably in folded-in position the first wing portions are enclosed by the second wing portions the advantage is achieved that a smaller displacement of the coupling means is necessary for folding out the wings.

If in further preference in folded-out position an angle smaller than 180° and greater than 90° is enclosed between both adjoining second wing portions, both second wing portions lie in reflex position inside both first wing portions in the folded-out position, thereby the second wing portions or their coupling to the coupling means do not touch the fundus of the uterus, whereby damage or perforation is avoided.

Optimal insertion of the uterine rotator into the uterus is obtained when in a folded-in position the wing more preferably lies enveloped within a rod. It is recommended for this purpose that the rod is provided with a recess for receiving a folded-in wing. For optimal insertion of the uterine end it is necessary for this purpose that in folded-in position the uterine end has a round, for instance oval and circular, shape in cross section.

According to a preferred embodiment the coupling means comprise a coupling element received in the hollow rod. According to a first embodiment the coupling element is a slide strip, according to another embodiment the coupling element is a threaded strip. For good positioning of the uterus into for example anteversion, even when the patient inadvertently lies too high on the operating table, it is recommended that the rod of the uterine rotator be curved in shape The rod is further preferably provided with at least one hinge whereby the uterine end can pivot an the front part of the uterus can be placed in front of the endoscope, If in further preference the hinge is located at a distance from the tip of the uterine end such that the pivot point lies at the height of the cervix of the uterus, parts located forwardly of the uterus can, by both retroflexion and anterioflexion, be optimally viewed with the endoscope and become accessible to surgical instruments. The pivoting movement can be performed transversely of as well as in the plane of the wing or wings and the coupling means, including the coupling element. If however the pivoting movement is followed by a rotation movement, a pivoting movement in the plane of the wing or wings and the coupling means takes preference from the point of view of surgical technique.

For optimal positioning of the uterus for the endoscope and surgical instruments, it is further recommended that the uterine end be connected rotatably via the rotation means to the control end. The advantage being that through a combination of retroflexion or anterioflexion and rotation through about 90°, the lateral uterine blood vessels can be placed in a posterior or anterior position, whereby the laparoscopic hysterectomy is facilitated considerably. The secondary openings in the abdominal wall for the instruments can moreover be arranged at a lower level, for instance below the so-called bikini line, whereby this surgical approach provides a considerable aesthetic advantage.

Instead of making use of a pivoting and rotation movement, it is also possible to use two pivoting movements directed transversely of each other.

For an easy dissection of the cervix and the uterine artery, it is recommended that a fornix presentor be guided along the rod of the uterine rotator.

The greatest problem in laparoscopic vaginal hysterectomy is bleeding from the uterine artery. Under laparoscopic control, however, it is safe and easy to clamp the uterine artery along the vaginal side whereby bleeding can be avoided. For this purpose the invention provides for the instrument set at least one pair of artery forceps provided with a handle and mutually reciprocating jaws which is inserted via the vaginal vault. The jaws are for example 1–3 cm long. The shaft of the artery forceps is preferably curved. The artery forceps according to the invention can thus be used in combination with the uterine rotator and can remain in place when the uterus is removed. An optimal pair of artery forceps is obtained if each of the jaws pivots around one of the hinge elements lying at a mutual distance.

The present invention further relates to the uterine rotator as described above, and to the artery forceps as described above, Other features of the instrument set for laparoscopic vaginal hysterectomy, in addition to the hysterectomy according to the invention, will be further described hereinafter in the light of a number of non-limiting embodiments and the operative technique, wherein reference is made to the annexed drawings.

DESCRIPTION OF THE PREFERRED EMBODIMENTS

Figures 1, 2, 3, 4, 5:
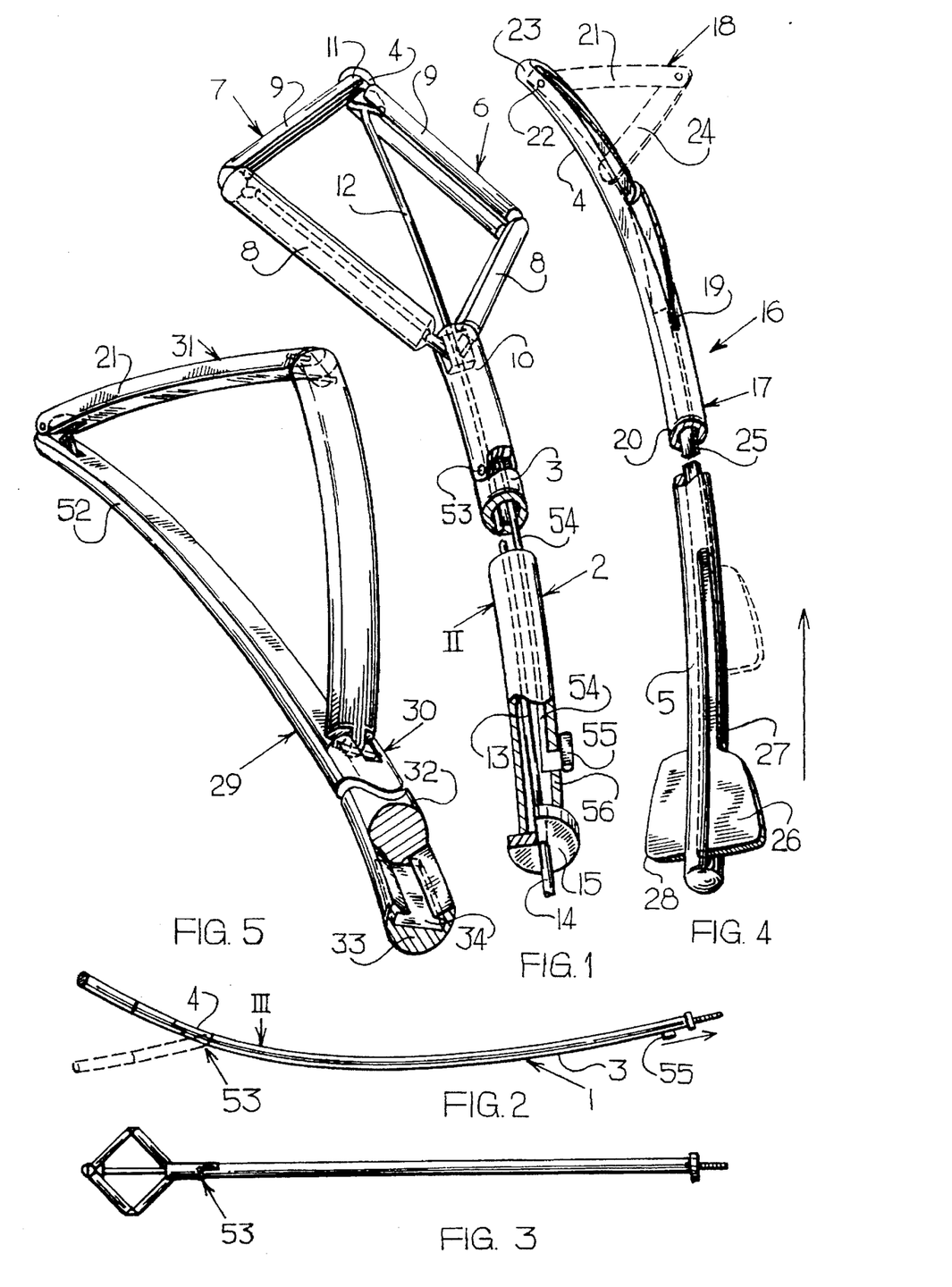
FIG. 1 is a perspective view, partially broken away of an embodiment of the uterine rotator of the instrument set according to the invention.
FIG. 2 is a side view of the invention shown in FIG. 1; as seen along arrow II.
FIG. 3 is a top view of the invention shown in FIG. 2; as seen along arrow III.
FIG. 4 is a perspective view, partially broken away, of an embodiment of the uterine rotator which has a single wing.
FIG. 5 is a perspective view, partially broken away, of the end of the uterine rotator shown in FIG. 4.

FIG. 1 shows an instrument set 1 according to the invention for laparoscopic vaginal hysterectomy. It is a uterine rotator 2 which comprises a hollow rod 3 with a uterine end 4 for insertion into the uterus and a control end 5. The uterine rotator 2 further comprises two wings 6 and 7 outwardly movable diametrically in relation to each other. Each wing 6 and 7 comprises a first wing portion 8 that pivotally connected to a rod tip 10, and a second wing portion 9 which on one side is pivotally connected to the first win portion 8 and on the other side via a hinge piece 11 to coupling means comprised of a flexible coupling element 12 and guided in the hollow rod, which coupling element 12 has the form of a threaded strip, for which purpose the free end 13 is provided with a thread 14 onto which a nut 15 is rotated and supported on the hollow rod 3. Using resetting means (not shown) the coupling element 12 is pressed to a position in which the wings 6 and 7 are folded inward. In inward folded position the uterine end 4 has a round cross section.

Figure 10:
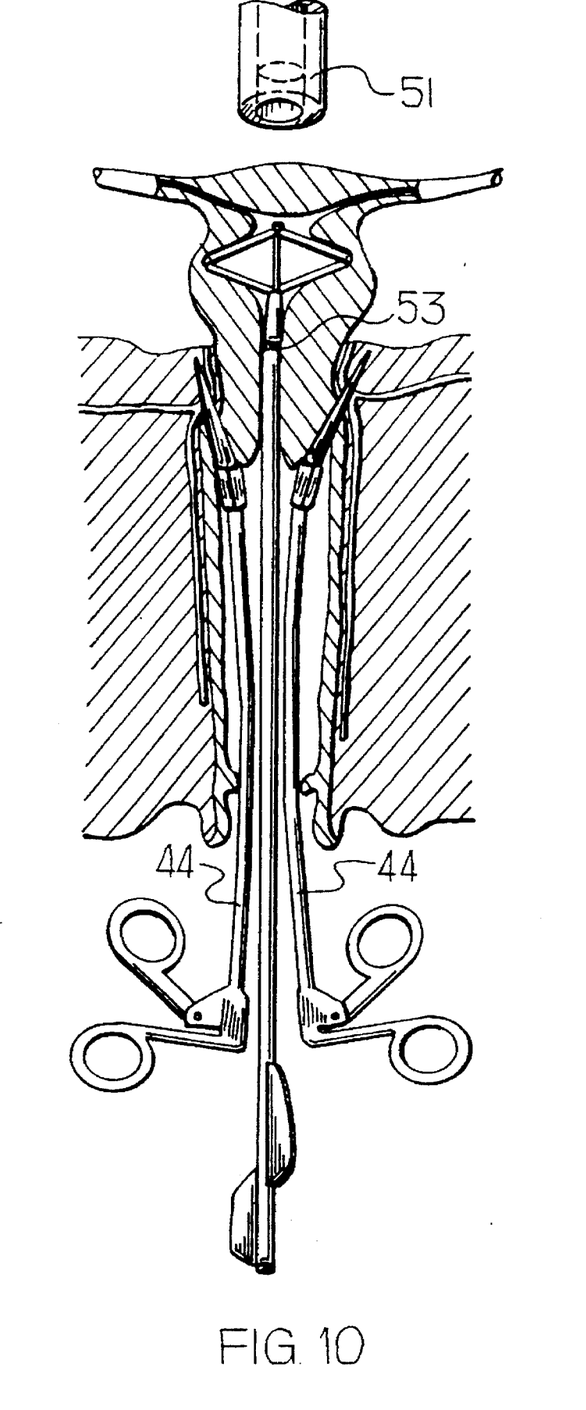
FIG. 10 is a schematic view of an operative technique for laparoscopic vaginal hysterectomy wherein the instrument set according to the invention is applied.

The hollow rod 3 is provided with a hinge 53 which can be actuated with a pivot rod 54 which is guided in the hollow rod 3 and ends in a control member 55 slidably guided in a slotted hole 56. The uterine end 4 can, as shown in FIG. 2, thus be pivoted downward through up to 70°, preferably through more than about 30°, whereby the ventral side of the uterus can be oriented toward the stationary endoscope 51 as shown in FIG. 10. For the sake of clarity FIG. 3 likewise shows the rotator 2 in top view.

FIG. 4 shows another instrument set 16 according to the invention which comprises a uterine rotator 17 which is provided with only one wing 18 which has substantially the same construction as the wings 6 and 7 of the rotator of FIG. 1. The uterine end 4 of the uterine rotator 17 is provided with an elongated recess 19 in which the folded-in wing 18 (drawn with continuous lines) can be received inside the imaginary envelope of the sectionally round rod 20. The wing 18 comprises a first wing portion 21 connected to the rod tip 23 via a hinge 22 situated in the recess 19. The other wing portion 24 is pivotally connected to a slide strip 25 guided in the hollow rod. Inward and outward folding of the wing 18 takes place by moving the slide strip 25 using a handle 26, which is guided in a recess 27, in the control end 5 which is further provided with a second handle 28.

FIG. 5 shows an instrument set 29 according to the invention which comprises a uterine rotator 30 with a single wing 31, the construction of which substantially corresponds with the wing 18 of FIG. 2. The wing portion 21 is however pivotally connected to a fork-like uterine end 52 and a slide strip 32 is guided in a guide path 34 arranged in a solid rod 33.

As is show in FIGS. 1, 4 and 5, the uterine rotators 2, 17 and 30 are preferably curved. The wings moreover each have a shape which enable good and certain contact with the uterine inner wall without causing great damage.

Figures 6, 7:
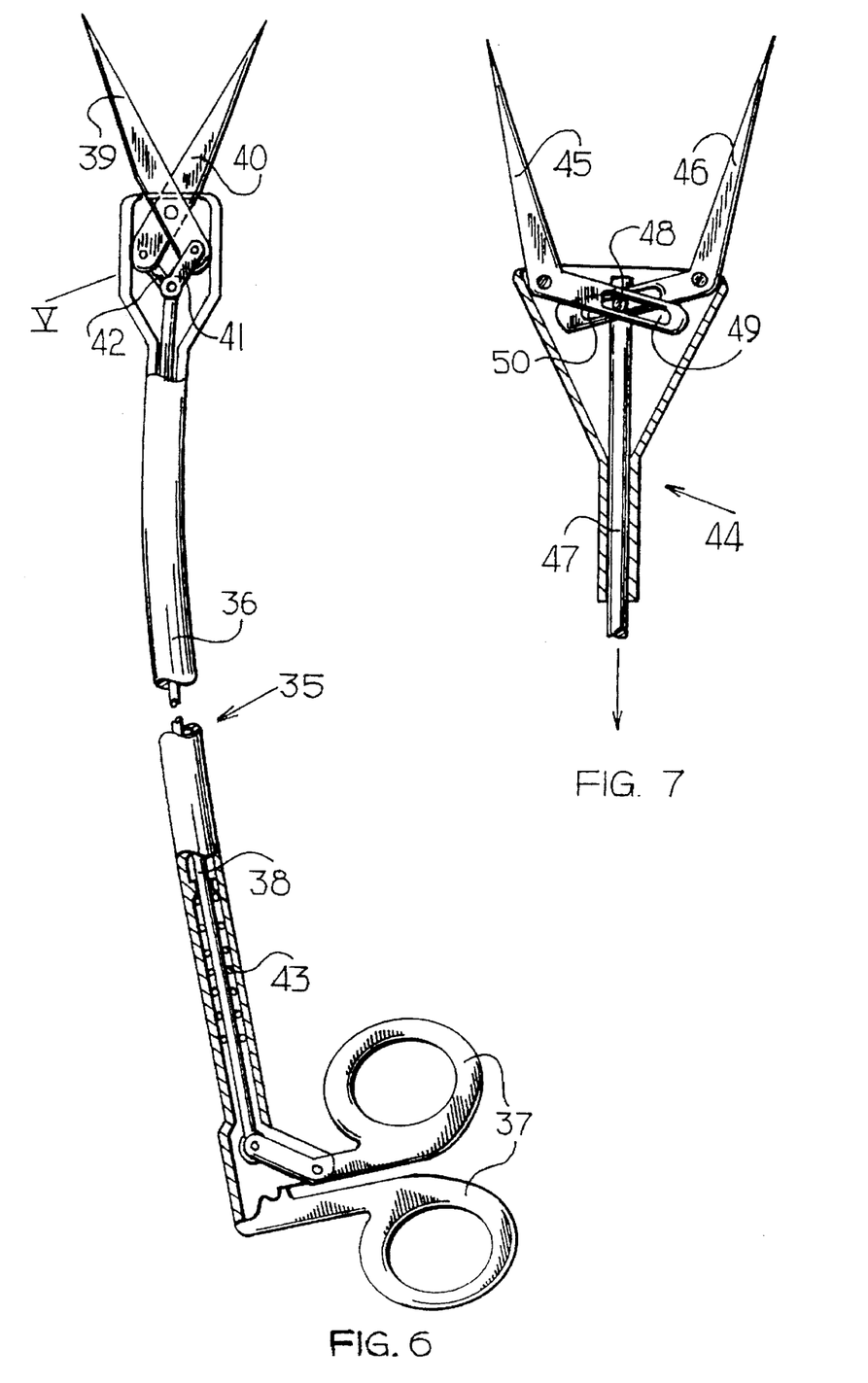
FIG. 6 is a partially broken away perspective view of a pair of artery forceps for the instrument set according to the invention.
FIG. 7 is an enlarged end view of a variation of the artery forceps shown in FIG. 6.

FIG. 6 shows a pair of artery forceps 35 for an instrument set according to the invention. The artery forceps 35 have a curved hollow shaft 36 in which a rod 38 is guided and controllable with finger grips 37. The rod 38 is coupled to both mutually reciprocating jaws 39 and 40 via the links 41 and 42 respectively. The jaws 39 and 40 are urged towards each other using a spring 43.

FIG. 7 shows another pair of artery forceps 44 according to the invention wherein the jaws 45 and 46 are movable with a rod 47 of which a pin 48 is received in slotted holes 49 and 50 respectively arranged in the angular jaws 45 and 46.

Figures 8, 9:
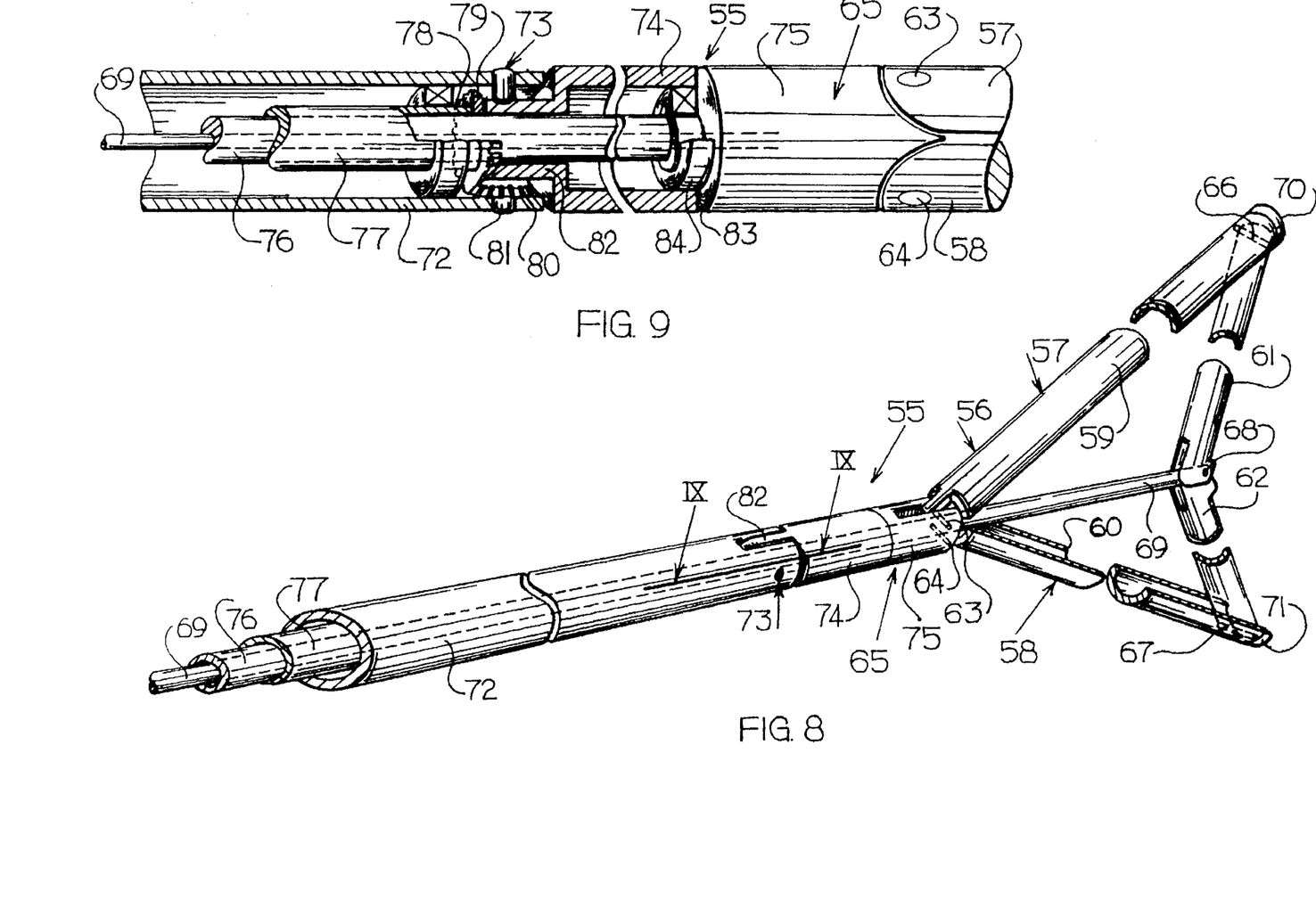
FIG. 8 is a perspective view, partially broken away, of an embodiment of the uterine rotator which has two wings.
FIG. 9 is a section taken along lines IX—IX in FIG. 8.

FIGS. 8 and 9 show another uterine rotator 55 according to the invention which likewise comprises a uterine end 56 for insertion into the uterus having two wings 57 and 58 which comprise semi-tubular first wing portions 59 and 60 which are hingedly connected to semi-tubular respective second wing portions 61 and 62. The first wing portions 59 and 60 are connected via a hinge 63, 64 to the rod 65 and on the other side via hinges 66, 67 to the second wing portions 61, 62 which are connected via a hinge 68 to the coupling means comprising a rod 69. The first wing portions 59 and 60 are provided on their free end with a cap part 70, 71.

Rod 65 is constructed from a rear end 72, a central portion 74 connected thereto via a hinge 73 and a rotatable forward portion 75.

Received coaxially in the hollow rear end 72 are the rod 69 for controlling the wings 57 and 58, a rotation tube 76 for causing the front portion 75 to rotate relative to the central portion 74 and a pivot tube 77 for causing the central portion 74 to pivot relative to the rear portion 72.

The pivot tube 77 comprises on its leading end 78 bevel gear 79 which co-acts with a bevel gear 80 fixed onto the pivot shaft 81 to which a part 82 of the central portion 74 inserted into the rear end 72 is non-releasably connected. Due to a rotation of pivot tube 77, the pivot shaft 81 will also rotate via the bevel gear par 79, 80, whereby the central portion 74 pivots independently of the rotation pivot tube 77.

Extending through the pivot tube 77, bevel gear 79 and the part 82 is the flexible rotation tube which is welded to an end wall 83 of the front portion 75 and which is mounted in the central portion 74 with an annular bearing 84.

It is thus possible from the control end of uterine rotator 55 to control the wings with the rod 69, to perform a rotation of the wings using the rotation tube 76 and to perform a pivoting movement of the front portion 75 via pivot tube 77.

FIG. 10 shows the operative technique with the uterine rotator of FIG. 1. A video endoscope 51 which is provided with a $CO_2$ laser (1060 sharplan, Laser Industry Limited, Tel Aviv, Israel), coupled to an operative laparoscope with an internal diameter of at least 7 mm (Stortz, Germany), which is equipped with persufflator (EP-A-0 350 499), whereby a constant pneumoperitoneum is made possible even during excessive aspiration, for example as a result of bleeding or after the vagina has been opened, is inserted via the abdominal wall to a position close to the uterus. Two or three additional working channels are further arranged in the abdomen.

The uterosacrals are then almost but not entirely transected and the douglas pouch incised up to the vaginal vault. If pelvic endometriosis is present this is first removed. The round ligaments are then coagulated, transected, the peritoneum is opened and the bladder moved aside. The ligamentum ovarium proprium is transected. Following dissection of the parametria, the uterine artery is clamped with an artery forceps according to the invention.

Hereafter the procedure continues as for a total or subtotal vaginal hysterectomy. The uterus is then sufficiently mobilized to subsequently perform a circular cervical incision even in nulligravidae. This automatically opens the douglas pouch. The uterosacral are grasped. The lower parametria can be easily grasped and transected. The uterus is then removed, the peritoneum closed, the parametria and the uterosacrals sutured and connected. Finally, the vaginal wall is closed.

FIGS. 11–15 show the operative technique using the uterine rotator as shown in FIGS. 8–10.

Figure 11:
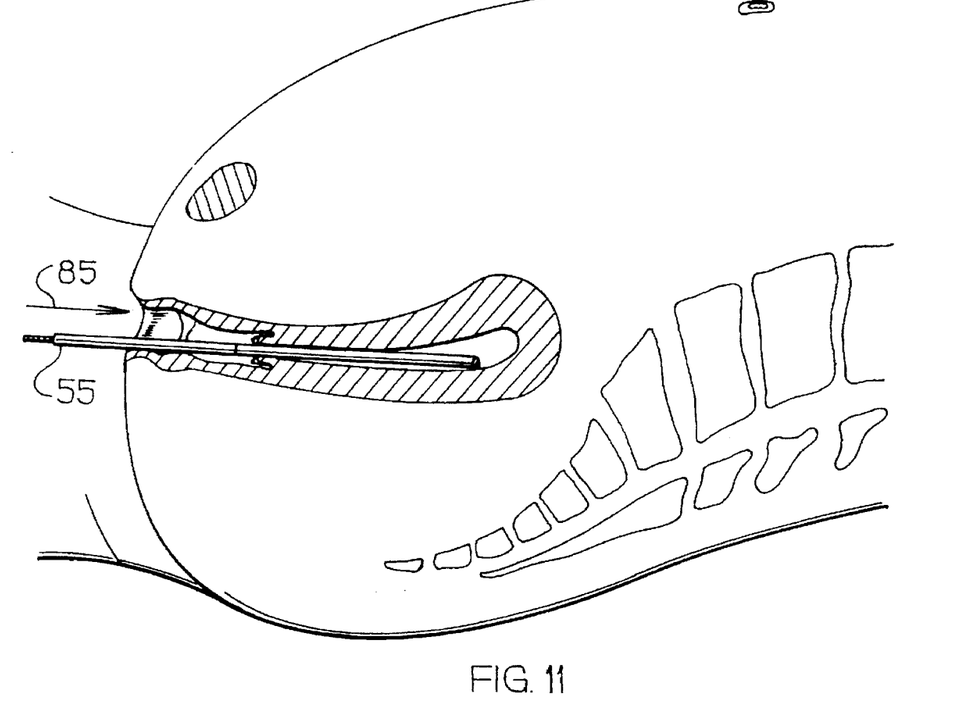
FIG. 11 is a side view showing a second operative technique for laparoscopic vaginal hysterectomy with a uterine rotator as according to FIGS. 8 and 9.
Figure 12:
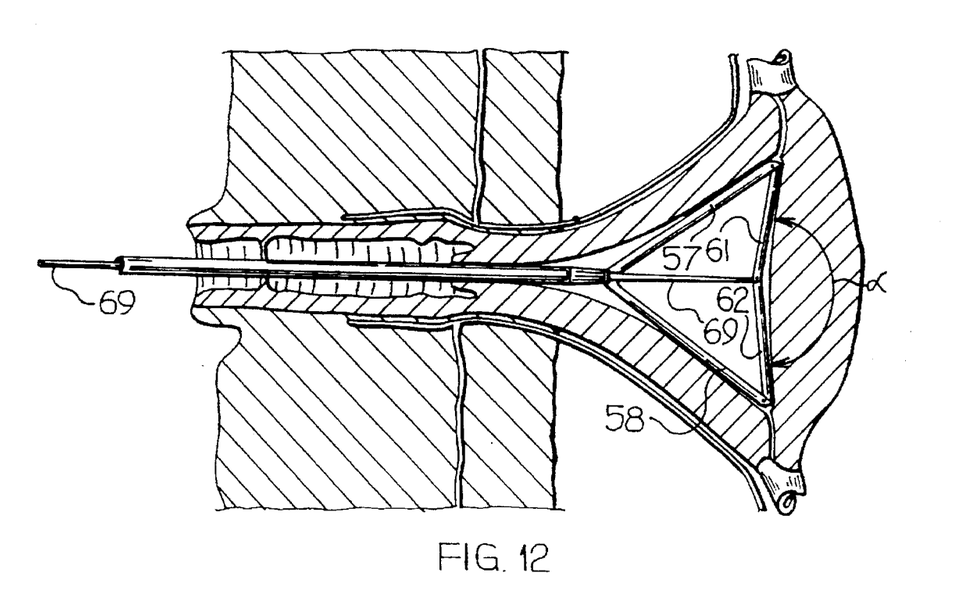
FIG. 12 is a top view showing a second operative technique for laparoscopic vaginal hysterectomy with the uterine rotator shown in FIGS. 8 and 9.

According to FIG. 11, the uterine rotator 55 is placed as according to arrow 85 into the uterus with folded-in wings as a cylindrical rod. FIG. 12 shows the situation after the wings 57 and 58 are spread by operating the rod 69. Here it can be seen that an angle $\alpha$ smaller than 180° but greater than 90° is enclosed between the second wing portions 61 and 62, so that the second wing portions 61 and 62 and rod 69 can make substantially no contact with the fundus of the uterus.

Figure 13:
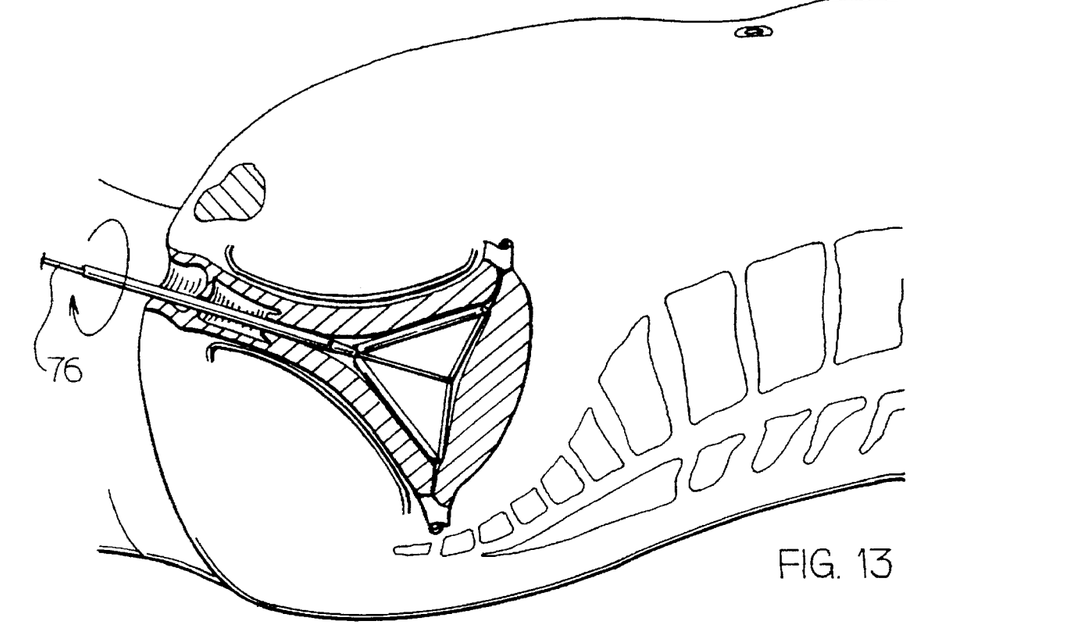
FIG. 13 is a side view, similar to FIG. 11, showing the uterine rotator rotating a uterus.
Figure 14:
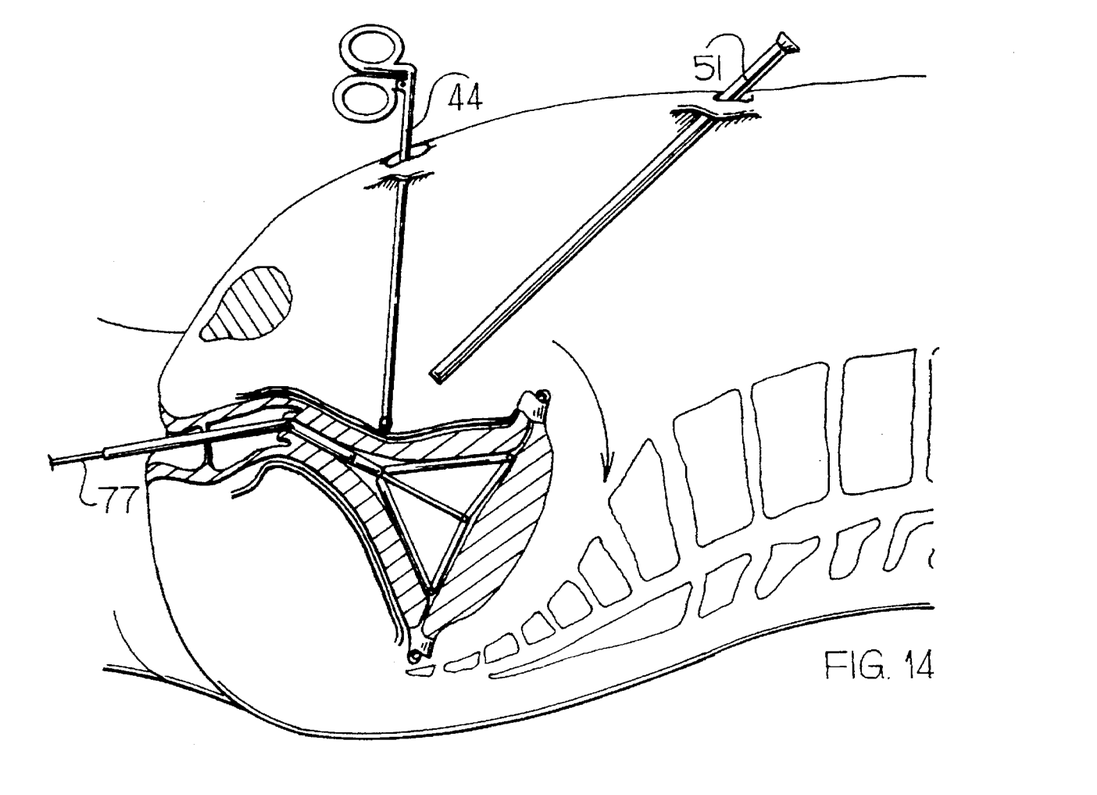
FIG. 14 is a side view, similar to FIGS. 11 and 13, showing a retroflexion-rotation approach in accordance with the operative techniques according to the invention.
Figure 15:
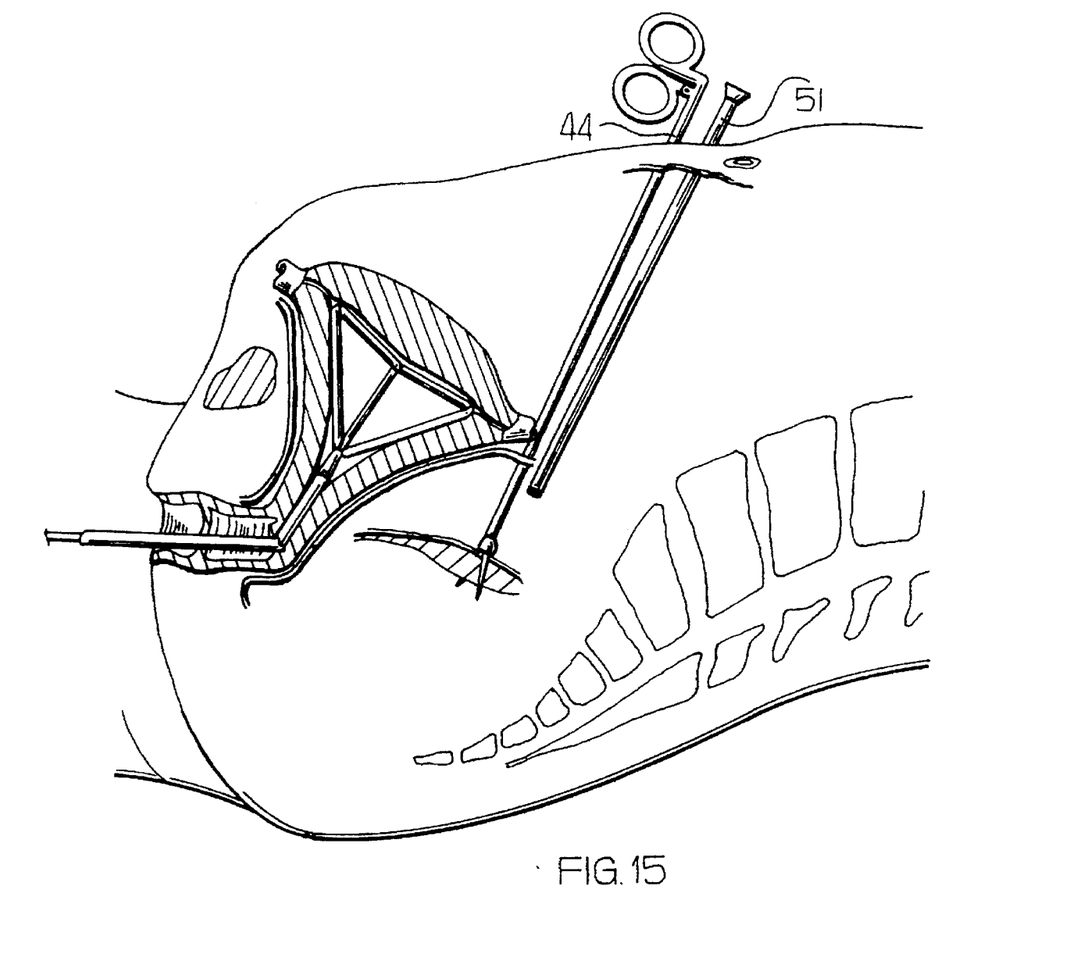
FIG. 15 is a side view, similar to FIGS. 11 and 13, showing an anterioflexion-rotation approach in accordance with the operative techniques according to the invention.

FIGS. 13 and 14 show in combination the retroflexion-rotation approach and FIGS. 13 and 15 show the anterioflexion-rotation approach in accordance with the operative technique according to the invention.

Through rotation of the rotation tube 76 from the situation shown in FIG. 11 the situation of FIG. 13 is reached, wherein the uterine blood vessels are now carried from lateral to anterior. In combination with a retroflexion by operating the pivot tube 77 the uterus is carried downward and the cervix upward, whereby the uterine artery becomes well visible to the endoscope 51 and becomes easily accessible to the artery forceps 44 and other instruments to be used.

In the anterioflexion according to FIGS. 13 and 15 the uterus is moved upward, whereby for instance large fibromas in posterior location become easily visible to the surgical instruments and the endoscope 51.

Figure 16:
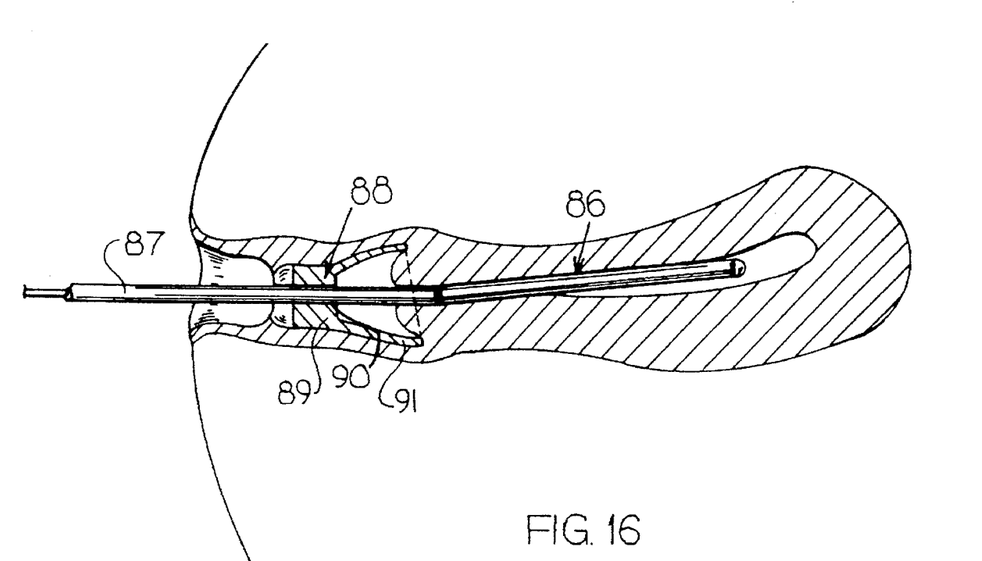
FIG. 16 is a view corresponding with FIG. 11 of another uterine rotator.
Figure 17:
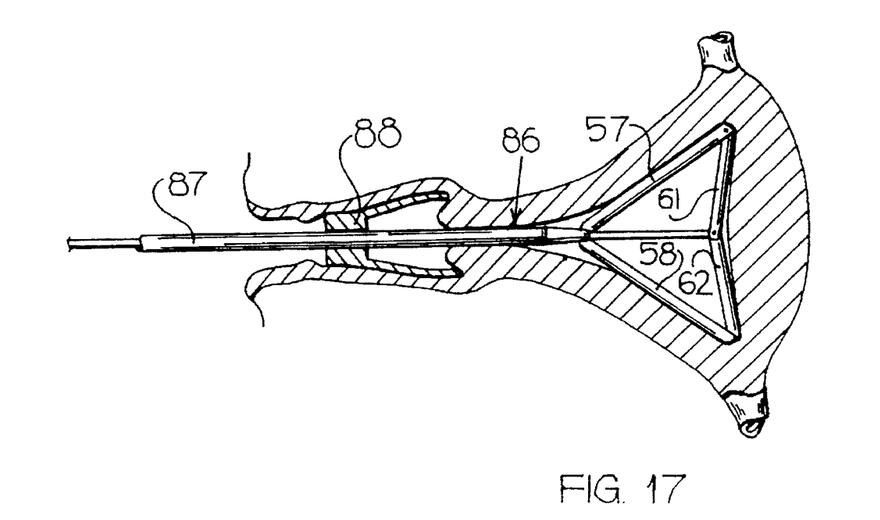
FIG. 17 is a side view corresponding with FIG. 12 of another uterine rotator.

FIGS. 16 and 17 show a uterine rotator 86 which is provided with a fornix presentor 88 which is slidable along the rod 87 and comprises a sleeve coupling 89 with a passage 90 through which passes the rod 87 and a collar 91 which diverges in the direction of the uterus and which grips over the cervix. Laparoscopic dissection of the cervix is thus simplified, a also, through localizing of the vaginal walls, is dissection of the uterine artery, namely the ramus vaginalis.

Because the instrument set according to the invention is used for laparoscopic vaginal hysterectomy, the time duration of the surgical procedure can remain limited (up to less than 60 minutes) to the time for a vaginal or abdominal hysterectomy. Blood loss is moreover greatly reduced, which is an indirect indication of a safer operation. However, the postoperative morbidity evaluated on the basis of the occurrence of bowel sounds is considerably lower (vaginal hysterectomy [VH] mean: 1.3 days, 25–70th percentile: 1–2 days; abdominal hysterectomy [AH] mean: 2.5 days, 25–70th percentile: 2–3 day). The hospital stay is shorter (VH 4.5 days as opposed to AH 7.3 days). No post operative complications have been noted.

What is claimed is:

1. An instrument for laparoscopic vaginal hysterectomy, comprising:
    a uterine rotator including a rod with a uterine end for insertion into uterus and a control end;
    coupling means;
    a control member; and
    at least one wing, with the at least one wing movable from a folded-in position in the uterine end to a folded-out position in which the at least one wing makes contact with an inner wall of the uterus and with the at least one wing connected by the coupling means to the control member located at the control end, and wherein the uterine end of the rod is rotatably connected to the control end of the rod by a rotation means.

2. The instrument as claimed in claim 1, wherein the rod is provided with two wings.

3. The instrument as claimed in claim 2, wherein the wings are movable outwardly from the rod diametrically in relation to each other.

4. The instrument as claimed in claim 2, wherein the rod includes a rod tip and wherein each wing includes a first wing portion and a second wing portion connected for mutual rotation, with the first wing portion rotatably connected to a rod tip and with the second wing portion connected to the coupling means.

5. The instrument as claimed in claim 4, wherein the first wing portions are enclosed by the second wing portions in the folded-in position.

6. The instrument as claimed in claim 4, wherein adjoining second wing portions are separated from each other by an angle between 90° and 180° in the folded-out position.

7. The instrument as claims in claim 1, wherein the uterine end of the rod is connected to the control end of the rod by a plurality of hinges moveable transversely of each other.

8. An instrument for laparoscopic vaginal hysterectomy, comprising:

a uterine rotator including a rod with a uterine end for insertion into a uterus and a control end;

coupling means;

a control member; and at least one wing, wherein the at least one wing is movable from a folded-in position in the uterine end to a folded-out position in which the at least one wing makes contact with an inner wall of the uterus, wherein the at least one wing is connected by the coupling means to the control member located at the control end and wherein the at least one wing is substantially enveloped within the rod in the folded-in position.

9. The instrument as claimed in claims 8, wherein the rod is provided with a recess for receiving the at least one wing in the folded-in position.

10. An instrument for laparoscopic vaginal hysterectomy, comprising:

a uterine rotator including a rod with a uterine end for insertion into a uterus and a control end;

coupling means;

a control member; and at least one wing, wherein the at least one wing is movable from a folded-in position in the uterine end to a folded-out position in which the at least one wing makes contact with an inner wall of the uterus, wherein the at least one wing is connected by the coupling means to the control member located at the control end and wherein the uterine end of the rod has a substantially round shape in the folded-in position of the at least one wing.

11. An instrument for laparoscopic vaginal hysterectomy, comprising:

a uterine rotator including a rod with a uterine end for insertion into a uterus and a control end;

coupling means;

a control member; and at least one wing, wherein the at least one wing is movable from a folded-in position in the uterine end to a folded-out position in which the at least one win makes contact with an inner wall of the uterus, wherein the at least one wing is connected by the coupling means to the control member located at the control end and wherein the coupling means include a coupling element in the rod.

12. An instrument for laparoscopic vaginal hysterectomy, comprising:

a uterine rotator including a rod with a uterine end for insertion into a uterus and a control end;

coupling means;

a control member; and at least one wing, wherein the at least one wing is movable from a folded-in position in the uterine end to a folded-out position in which the at least one wing makes contact with an inner wall of the uterus, wherein the at least one wing is connected by the coupling means to the control member located at the control end and wherein the uterine end of the rod is connected by at least one hinge to the control end of the rod.

13. The instrument as claimed in claim 12, wherein the hinge is located at a distance from the uterine end such that a pivot point of the rod is located substantially adjacent the cervix of the uterus when the rod is inserted into the uterus.

14. The instrument as claimed in claim 12, wherein the rod is configured such that a pivoting movement takes place immediately forward of the at least one wing.

15. An instrument for laparoscopic vaginal hysterectomy, comprising:

a uterine rotator including a rod with a uterine end for insertion into a uterus and a control end;

coupling means;

a control member; and at least one win, wherein the at least one wing is movable from a folded-in position in the uterine end to a folded-out position in which the at least one wing makes contact with an inner wall of the uterus, wherein the at least one win is connected by the coupling means to the control member located at the control end and wherein the uterine rotator is provided with a for nix presenter guided on the rod.

16. An instrument set for laparoscopic vaginal hysterectomy which comprises: (a) a uterine rotator, including: a rod with a uterine end for insertion into a uterus and a control end; and at least one wing moveable from a folded-in position in the uterine end to a folded-out position in which the at least one wing makes contact with an inner wall of the uterus, wherein the at least one wing is connected by coupling means to a control member located at the control end, and (b) a pair of artery forceps provided with a handle and a plurality of mutually reciprocating jaws.

17. The instrument set as claimed in claim 16, wherein the artery forceps includes a curved shaft.

18. The instrument set as claimed in claim 1, wherein each of the jaws pivots on a hinge element lying at a mutual distance.

* * * * *

UNITED STATES PATENT AND TRADEMARK OFFICE
CERTIFICATE OF CORRECTION

PATENT NO. : 5,662,676  
DATED : September 2, 1997  
INVENTOR(S) : Philippe Robert Koninckx Page 1 of 3

It is certified that error appears in the above-identified patent and that said Letters Patent is hereby corrected as shown below:

Title Page, under [56] References Cited, U.S. PATENT DOCUMENTS, insert:
--3,299,883   1/1967    Rubens        128/4
  3,877,433   4/1975    Librach       128/303R--.

Title Page, under [56] References Cited, FOREIGN PATENT DOCUMENTS, insert:
--2506471     8/1975    Germany
  3020662    12/1981    Germany
    44877     2/1982    European Pat. Off.
   306123     3/1989    European Pat. Off.
  WO8911827  12/1989    WIPO
   464463     1/1992    European Pat. Off.--.

Column 1 Line 14 delete "SUMMARY OF THE INVENTION" and substitute therefor: --2. Description of the Prior Art--.

Column 1 Line 24 "Surgery" should read --surgery--.

Column 1 before Line 39 insert --SUMMARY OF THE INVENTION--.

Column 1 Line 49 "which connected" should read --which is connected--.

Column 1 Line 62 "pro-operative" should read --pre-operative--.

Column 2 Line 29 after "shape" insert a period --.--.

Column 2 Line 31 "an the front" should read --and the front--.

Column 3 Lines 25-26, under FIG. 2, between "FIG. 1" and "as seen" delete semicolon --;--.

Column 3 Line 26, after "along arrow II", delete period --.-- and insert semicolon --;--.

Column 3 Lines 27-28, under FIG. 3, between "FIG. 2" and "as seen" delete semicolon --;--.

UNITED STATES PATENT AND TRADEMARK OFFICE
CERTIFICATE OF CORRECTION

PATENT NO. : 5,662,676
DATED : September 2, 1997
INVENTOR(S) : Philippe Robert Koninckx Page 2 of 3

It is certified that error appears in the above-identified patent and that said Letters Patent is hereby corrected as shown below:

Column 3 Line 28, after "along arrow III" delete period --.-- and insert semicolon--;--.

Column 3 Line 41, under FIG. 9, after "in FIG. 8" delete period --.-- and insert semicolon --;--.

Column 4 Line 5 after "that" insert --is--.

Column 4 Line 8 "win portion" should read --wing portion--.

Column 4 Line 29 after "rotator" insert --2--.

Column 4 Line 48 "As is show" should read --As is shown--.

Column 4 Line 50 "enable" should read --enables--.

Column 5 Line 17 after "end 78" insert --a--.

Column 5 Line 23 "gear par" should read --gear pair--.

Column 5 Line 24 after "rotation" insert --of--.

Column 5 Line 38 after "equipped with" insert --a--.

Column 5 Line 58 "uterosacral" should read --uterosacrals--.

Claim 1 Column 6 Line 49 "into uterus" should read --into a uterus--.

Claim 7 Column 7 Line 10 "as claims" should read --as claimed--.

Claim 9 Column 7 Line 28 "in claims 8" should read --in claim 8--.

Claim 11 Column 7 Line 55 "at least one win" should read --at least one wing--.

UNITED STATES PATENT AND TRADEMARK OFFICE
CERTIFICATE OF CORRECTION

PATENT NO. : 5,662,676
DATED : September 2, 1997
INVENTOR(S) : Philippe Robert Koninckx It is certified that error appears in the above-identified patent and that said Letters Patent is hereby corrected as shown below:

Claim 15 Column 8 Line 33 "at least one win" should read --at least one wing--.

Claim 15 Column 8 Line 37 "at least one win" should read --at least one wing--.

Claim 15 Column 8 Line 39 "for nix" should read --fornix--.

Claim 16 Column 8 Lines 41-42 after "hysterectomy" insert --,--.

Claim 18 Column 8 Line 53 "claimed in claim 1" should read --claimed in claim 16--.

Signed and Sealed this

Twenty-sixth Day of May, 1998

Attest:

BRUCE LEHMAN

Attesting Officer

Commissioner of Patents and Trademarks